(12) United States Patent
Ogawa

(10) Patent No.: US 6,937,268 B2
(45) Date of Patent: Aug. 30, 2005

(54) ENDOSCOPE APPARATUS

(75) Inventor: Kiyotomi Ogawa, Hachioji (JP)

(73) Assignee: Olympus Corporation, Tokyo (JP)

(*) Notice: Subject to any disclaimer, the term of this patent is extended or adjusted under 35 U.S.C. 154(b) by 531 days.

(21) Appl. No.: 10/091,893

(22) Filed: Mar. 6, 2002

(65) Prior Publication Data

US 2002/0137986 A1 Sep. 26, 2002

(30) Foreign Application Priority Data

Sep. 1, 1999 (JP) ..................... H11-247588

(51) Int. Cl.[7] .................................. H04N 7/18
(52) U.S. Cl. ................ 348/65; 356/241; 600/117
(58) Field of Search ............... 348/65, 141, 251, 348/355; 385/116; 356/241.1; 600/118, 117, 101, 166

(56) References Cited

U.S. PATENT DOCUMENTS

| | | | | |
|---|---|---|---|---|
| 5,070,401 A | * | 12/1991 | Salvati et al. | 348/141 |
| 5,469,254 A | * | 11/1995 | Konomura | 356/241.1 |
| 5,675,380 A | * | 10/1997 | Florent et al. | 348/251 |
| 5,818,527 A | * | 10/1998 | Yamaguchi et al. | 348/335 |
| 6,063,023 A | | 5/2000 | Sakiyama et al. | |
| 6,301,416 B1 | * | 10/2001 | Okano et al. | 385/116 |

FOREIGN PATENT DOCUMENTS

| | | |
|---|---|---|
| JP | 6-339454 | 12/1994 |
| JP | 8-12332 | 2/1996 |
| JP | 2778739 | 5/1998 |

* cited by examiner

Primary Examiner—Gims Philippe
(74) Attorney, Agent, or Firm—Scully, Scott, Murphy & Presser

(57) ABSTRACT

An imaging unit including a pair of objective lens systems and an imaging device that photoelectrically converts optical images into image signals is incorporated in the distal portion of an endoscope. The pair of objective lens systems is arranged to pick up images while viewing an object from different viewing points. Optical images having traveled through the objective lens systems are converged on the imaging device. A camera control unit converts image signals, which result from photoelectric conversion performed by the imaging device, into video signals according to which images are displayed on a monitor. A video capture circuit converts the produced video signals into digital image signals. A host computer performs arithmetic operations using the resultant digital image signals. A desired cutting plane is designated using the reference image displayed on the monitor, whereby section information concerning a viewer's desired section determined with the cutting plane can be acquired.

13 Claims, 16 Drawing Sheets

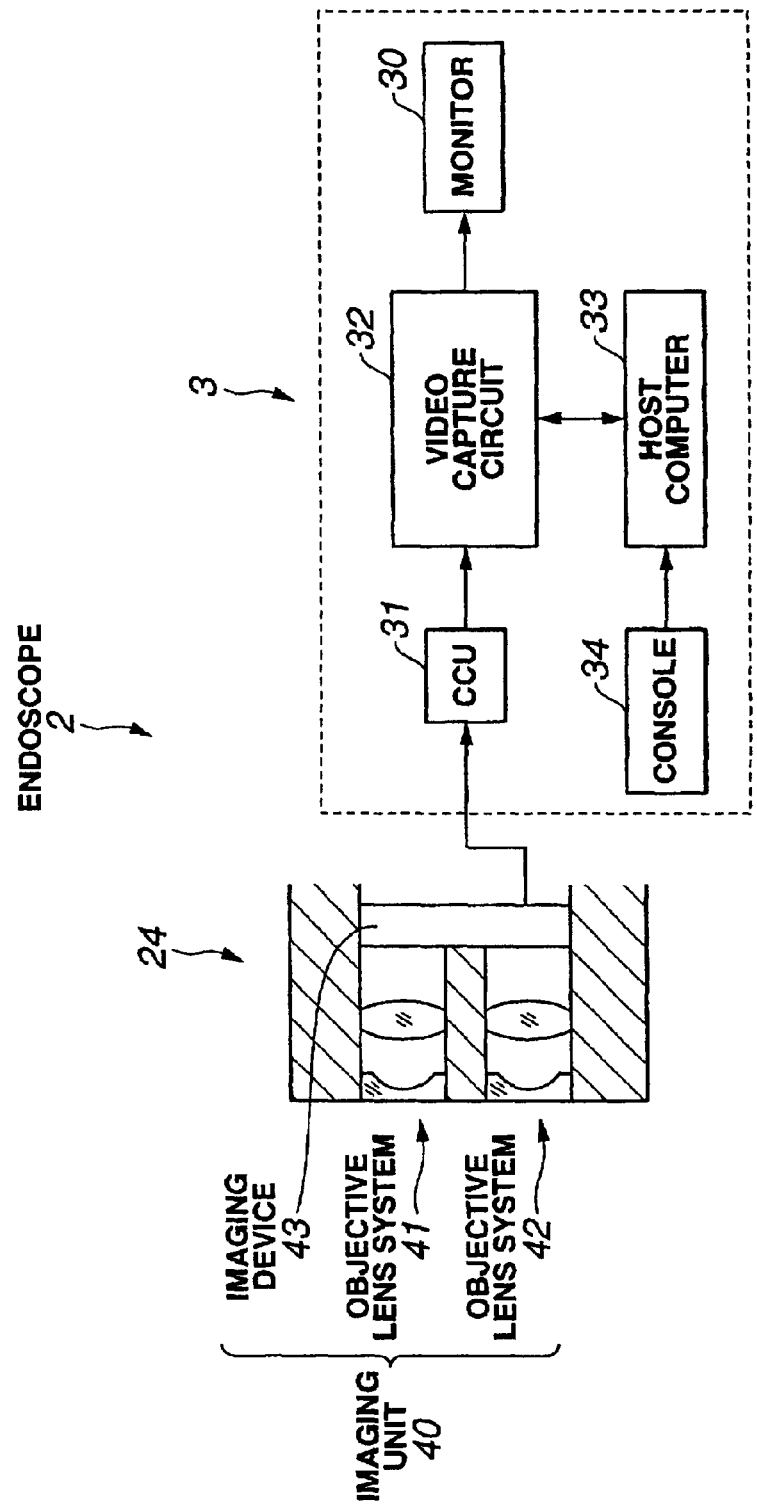

ENDOSCOPE APPARATUS

The present application claims the benefit of Japanese Patent Application No. Heisei 11-247588 filed in Japan on Sep. 1, 1999, the contents of which are incorporated by reference.

BACKGROUND OF THE INVENTION

1. Field of the Invention

The present invention relates to an endoscope system for assisting in objectively assessing the outline of a section of an object, which lies at a desired cutting position, using image signals that represent images picked up by viewing the object from a plurality of viewing points.

2. Description of the Related Art

In recent years, endoscopes have been widely employed in the fields of medicine and industries. Generally, an object appears planar in a view image picked up by an ordinary endoscope. It is therefore hard to identify the irregularity or the like in the surface of the object.

Therefore, for example, Japanese Examined Patent Application Publication No. 8-12332 describes a measuring endoscope system for three-dimensionally measuring an object using images picked up by viewing the object from a plurality of viewing points. Moreover, Japanese Patent Gazette No. 2778739 describes a measuring endoscope system that indicates a distance from a reference plane to a measuring point when the reference plane and measuring point are designated, enabling a user to objectively recognize the height or depth of a convex or concave part of an object.

Conventional measuring endoscope systems can measure three coordinates that represent in three-dimensional space a point designated in a reference image, a distance between two points, or a depth from a designated plane.

However, the conventional measuring endoscope systems request a user to designate a plurality of points, and infer the three-dimensional shape of an object of observation from three coordinates that represent each of the points. This poses a problem that it is hard to intuitively grasp the three-dimensional outline of the object of observation.

Moreover, the conventional measuring endoscope systems may adopt a method of acquiring three-dimensional information concerning an entire imaging range from image information so as to create a three-dimensional model. However, this poses a problem that it takes too much time for a computer to perform arithmetic operations required to create the three-dimensional model, making the method is impractical.

Therefore, when the depth of an object, for example, a corroded portion of the inner wall of a pipe must be measured, it takes much time to identify the deepest point.

SUMMARY OF THE INVENTION

An object of the present invention is to provide an endoscope system that acquires section information concerning a viewer's desired cutting plane when the desired cutting plane is designated using a displayed reference image.

In short, an object of the present invention is to provide an endoscope system that makes it easy to designate a cutting plane whose measurement is desired, and assists in grasping the outline of a section of an object of observation, that is, the outline of the designated cutting plane.

According to the present invention, there is provided an endoscope system having an imaging unit that picks up images of an object of observation while viewing the object of observation from a plurality of viewing points. Image signals representing the images, which the imaging unit has picked up while viewing the object of observation from the viewing points, are subjected to image processing and arithmetic operations, whereby stereo measurement is achieved.

The endoscope system consists mainly of a corrected image producing means, an image displaying means, a cutting-plane reference line designating means, a corresponding point searching means, a section information arithmetic means, and a section information outputting means. Herein, the corrected image producing means adopts one of the images picked up by viewing the object of observation from the plurality of viewing points as a reference image, and regards the other image as a comparison image. The corrected image producing means corrects optical deformations in the reference image and comparison image so as to produce a corrected reference image and corrected comparison image. Among the reference image, comparison images, corrected reference image, and corrected reference images, the image displaying means displays at least the reference image or corrected reference image on a screen. The cutting-plane reference line designating means is used to draw a cutting-plane reference line, which specifies a cutting-plane position that determines a section of the object of observation whose section information should be acquired, in an image displayed on the screen. The corresponding point searching means regards a point on the reference cutting-plane line in the corrected reference image as a point of attention, and searches the corrected comparison image for a corresponding point that is associated with the point of attention. The section information arithmetic means calculates three coordinates, which represent a point in three-dimensional space whose mapping results in a point of attention on the cutting reference line according to the principles of trigonometrical measurement, using the position of the point of attention in the corrected reference image and the position of the corresponding point in the corrected comparison image searched for by the corresponding point searching means. The section information arithmetic means thus acquires section information concerning the section of the object of observation determined with the cutting-plane position. The section information outputting means provides the section information using values calculated by the section information arithmetic means.

The above and other objects of the present invention, and the features and advantages thereof will be more clearly understood from the subsequent description made in reference to the accompanying drawings.

BRIEF DESCRIPTION OF THE DRAWINGS

FIG. 1 to FIG. 15 are concerned with an embodiment of the present invention;

FIG. 1 is an explanatory diagram schematically showing the configuration of an endoscope system capable of performing measurement;

FIG. 2 is an explanatory diagram for explaining an imaging unit incorporated in the distal portion of an inserting section of an endoscope and a measuring device having an arithmetic unit;

FIG. 3 shows a scene where an object-of-observation region is observed using an endoscope;

FIG. 4 is a flowchart describing stereo measurement;

FIG. 5 shows an example of an endoscopic image and a cutting-plane reference line displayed on the screen of a monitor by means of a reference image displaying means;

FIG. 6 is an explanatory diagram showing a cutting plane and a sectional contour line;

FIG. 7 is an explanatory diagram showing another example of a reference line;

FIG. 8 shows an example of a sectional contour line displayed as section information;

FIG. 9 is an explanatory diagram showing an example of a sectional contour line displayed while being superposed on a reference image;

FIG. 10 is an explanatory diagram showing a camera coordinate system defined in order to present section information;

FIG. 12 shows another example of a sectional contour line displayed as section information;

FIG. 13 shows still another example of a sectional contour line displayed as section information;

FIG. 14 is a flowchart describing an algorithm for searching for a corresponding point;

FIG. 15 is an explanatory diagram concerning monitor screen images displayed after searching for a corresponding point is completed;

FIG. 16 is an explanatory diagram showing images displayed on the screen of a monitor;

FIG. 17 is a flowchart describing a method of improving precision in section information by utilizing the order of points juxtaposed along a reference line;

FIG. 18 is a flowchart describing a method of improving precision in section information by utilizing the depths of surrounding points;

FIG. 19 is a flowchart describing a method of improving precision in section information by utilizing a back-corresponding point;

FIG. 20 is a flowchart describing a method of improving precision in section information by utilizing the magnitude of deviation from an epi-polar line;

FIG. 21 is a flowchart describing a method of improving precision in section information by utilizing a differential coefficient;

FIG. 22 shows the shapes of small domains each defined to contain a point of attention;

DESCRIPTION OF THE PREFERRED EMBODIMENTS

Embodiments of the present invention will be described with reference to the drawings below.

Figure 1:
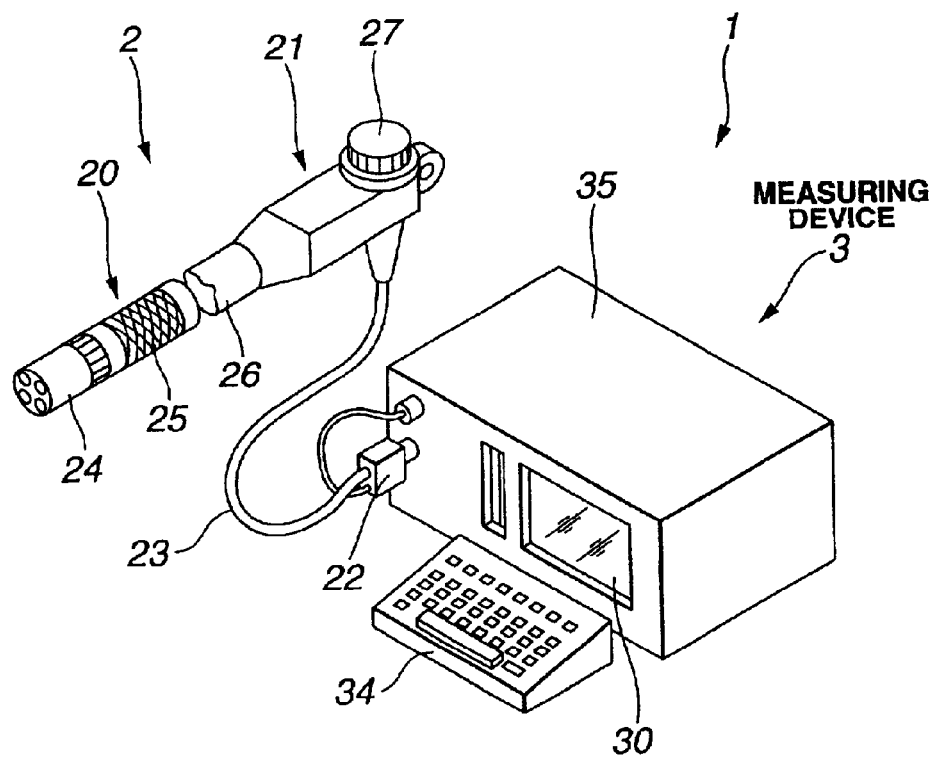
Figure 3:
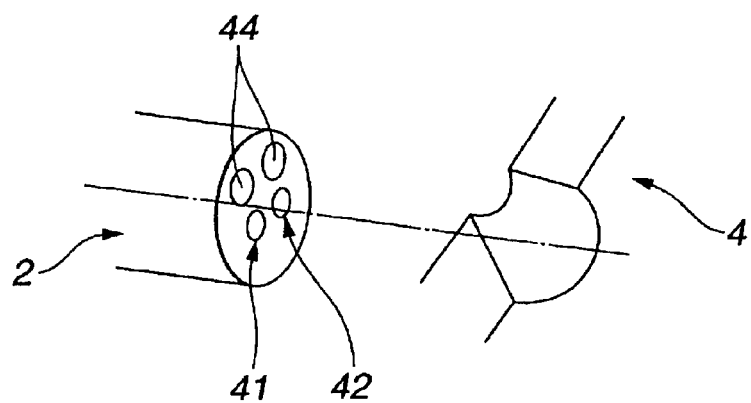
Figure 4:
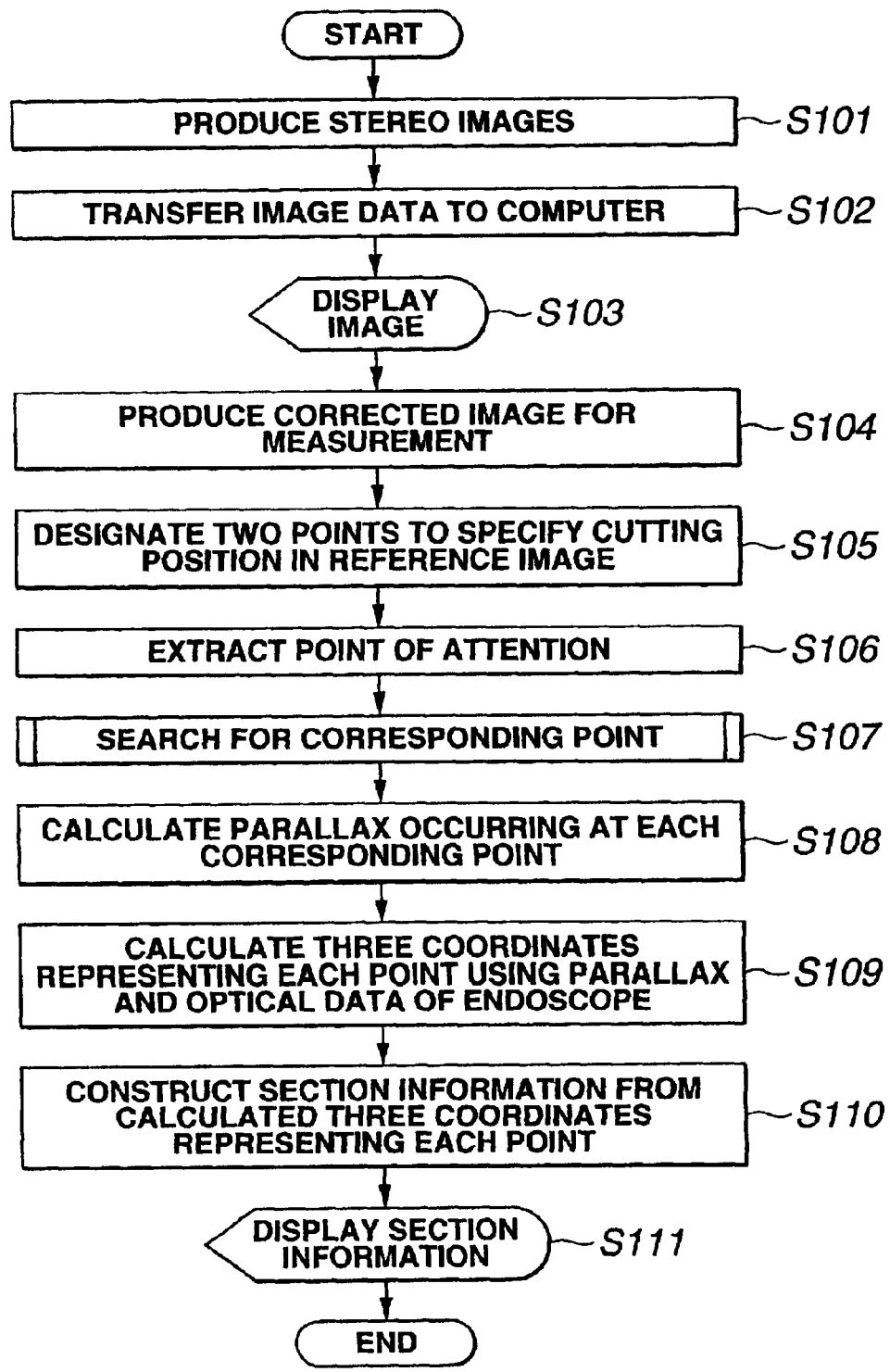
Figure 5:
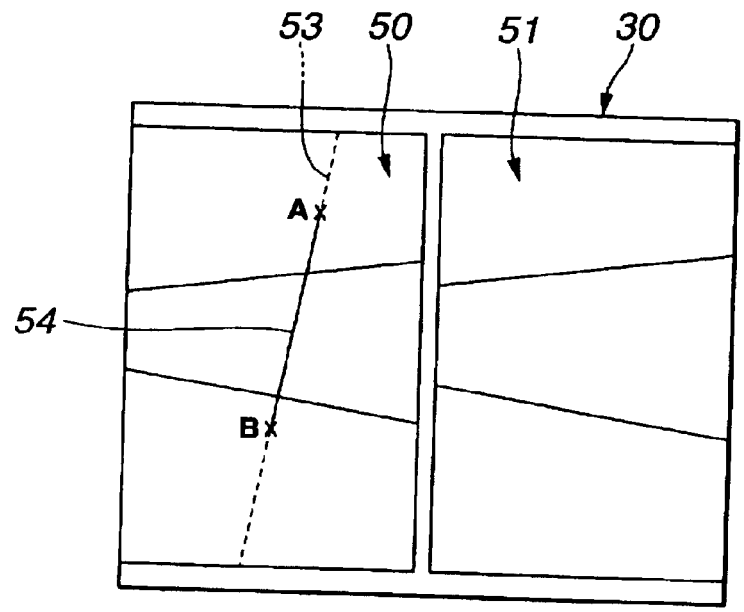
Figure 6:
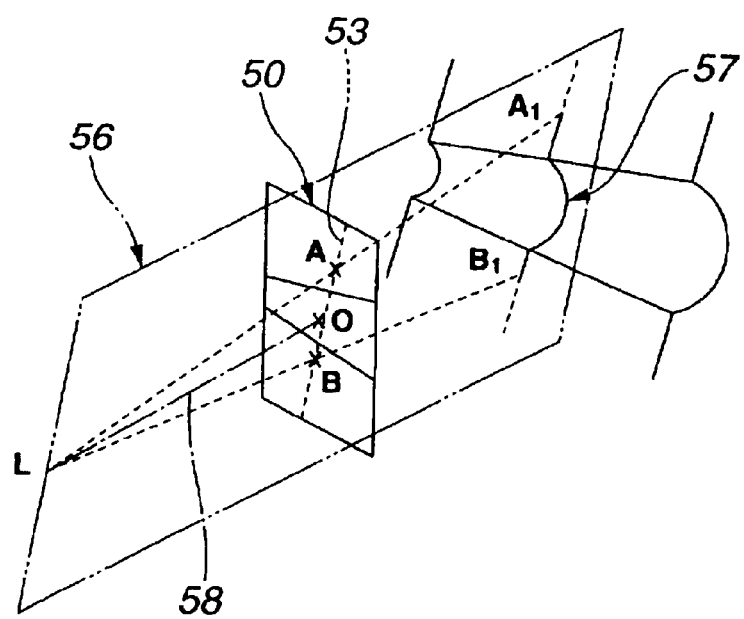
Figure 7:
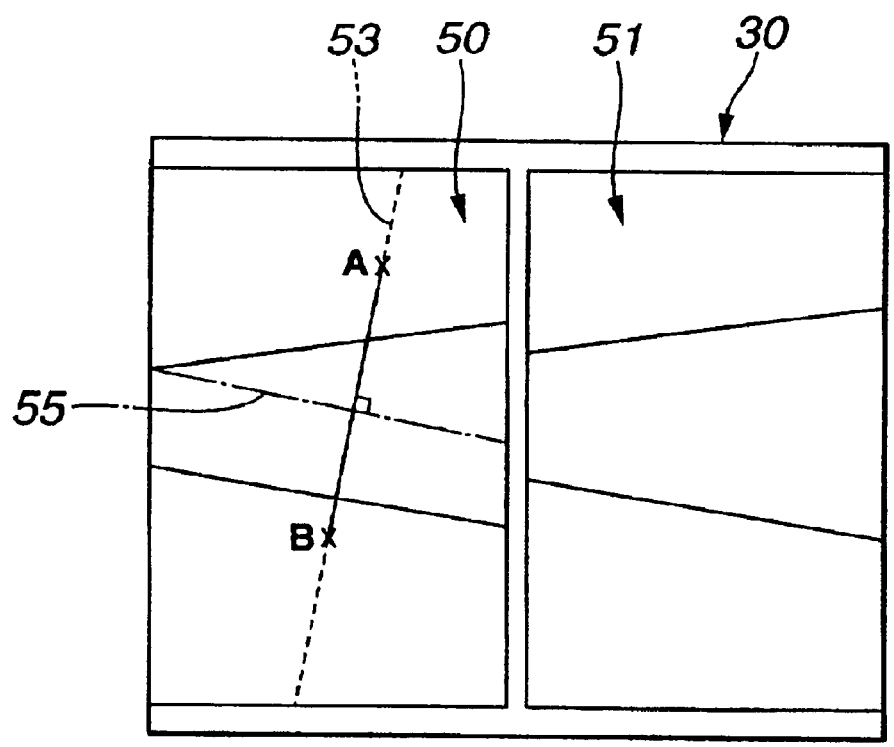
Figure 8:
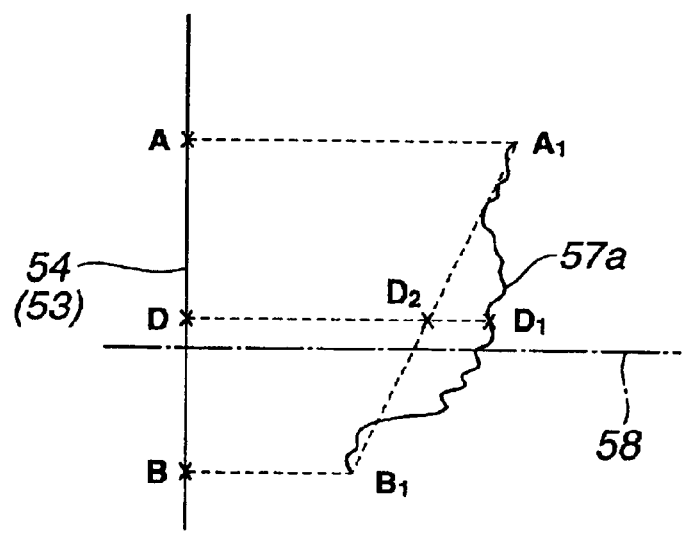
Figure 9:
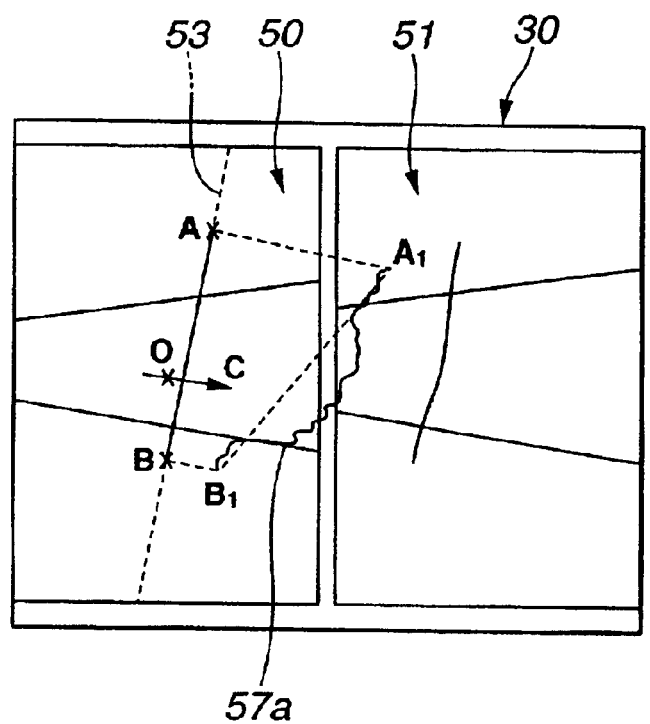
Figure 10:
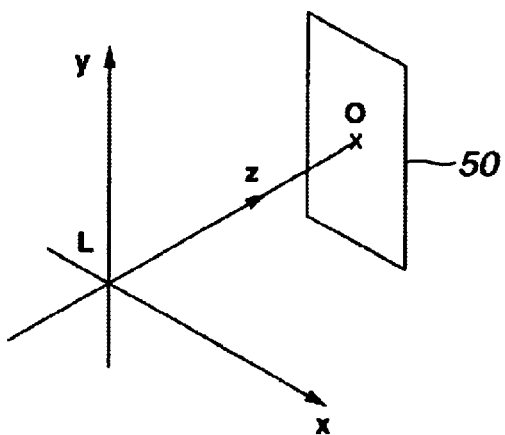
Figure 11A:
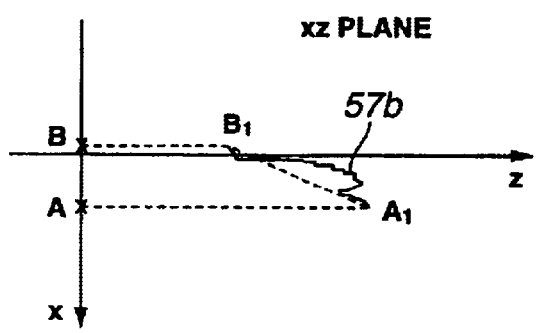
FIG. 11A shows another example of a sectional contour line displayed as section information projected on the xz plane.
Figure 11B:
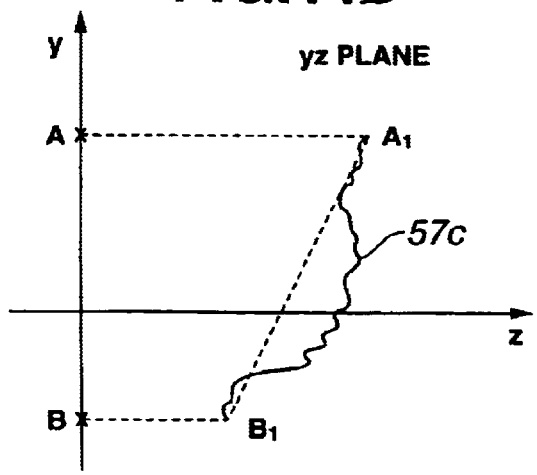
FIG. 11B shows another example of a sectional contour line displayed as section information projected on the yz plane.
Figure 12:
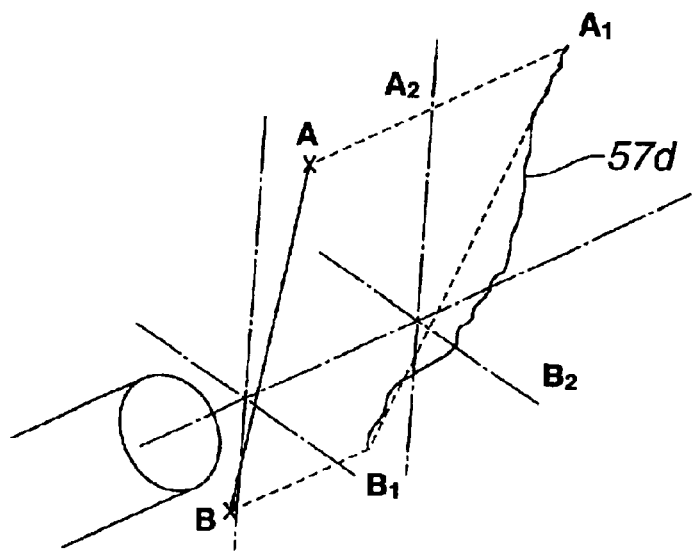
Figure 13:
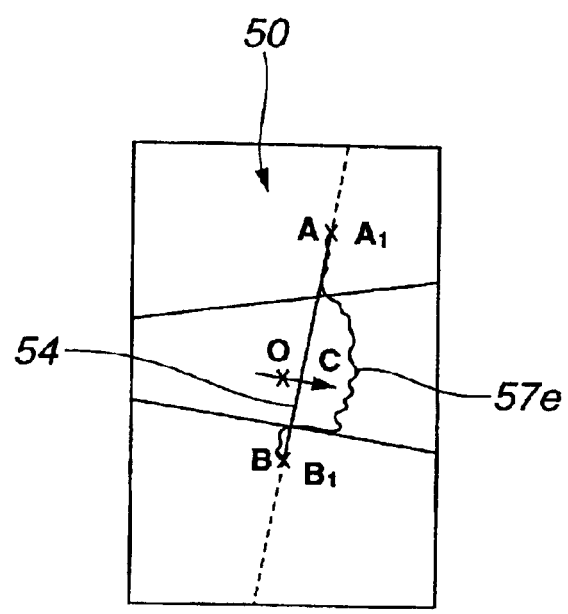
Figure 14:
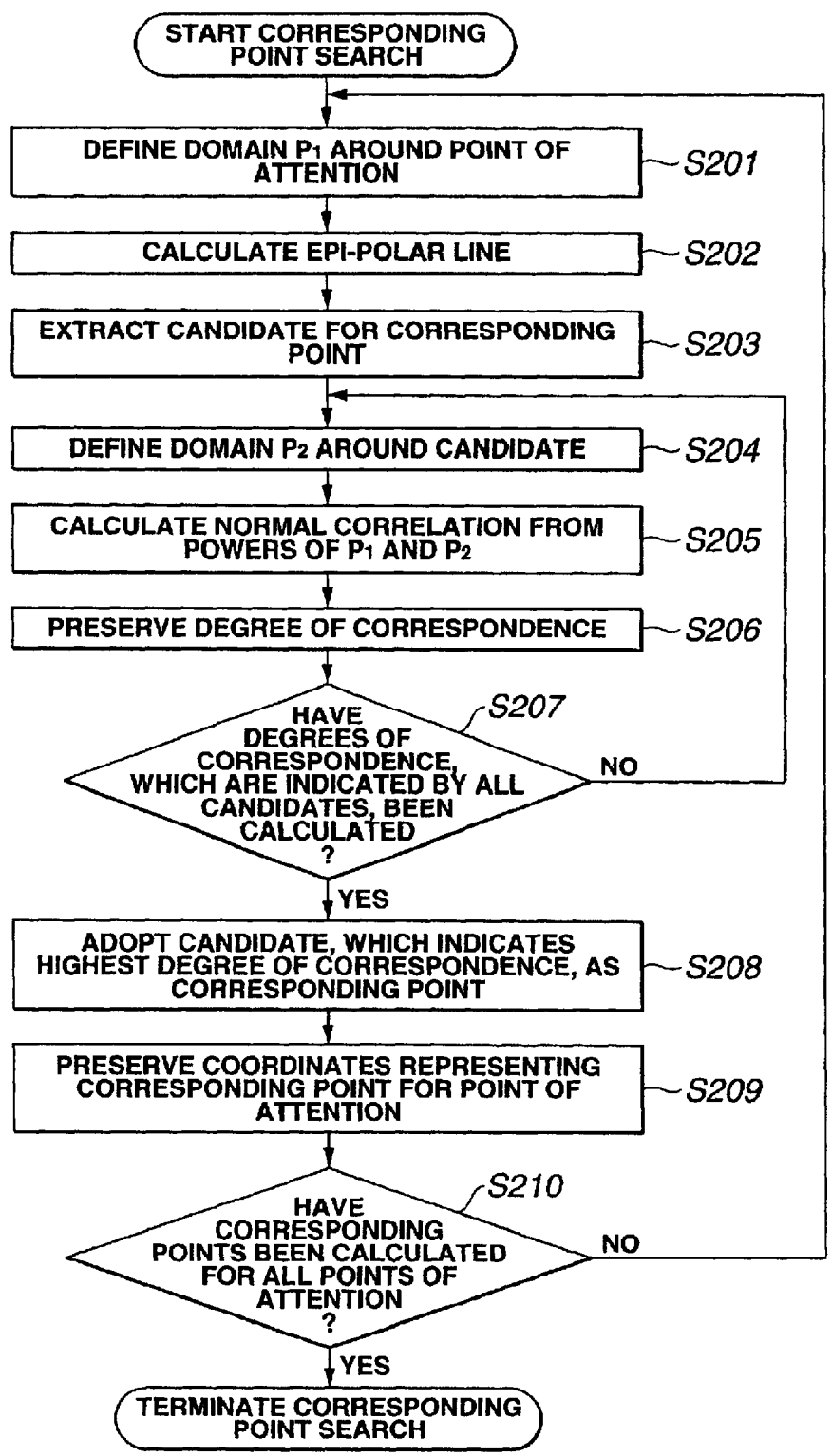
Figure 15:
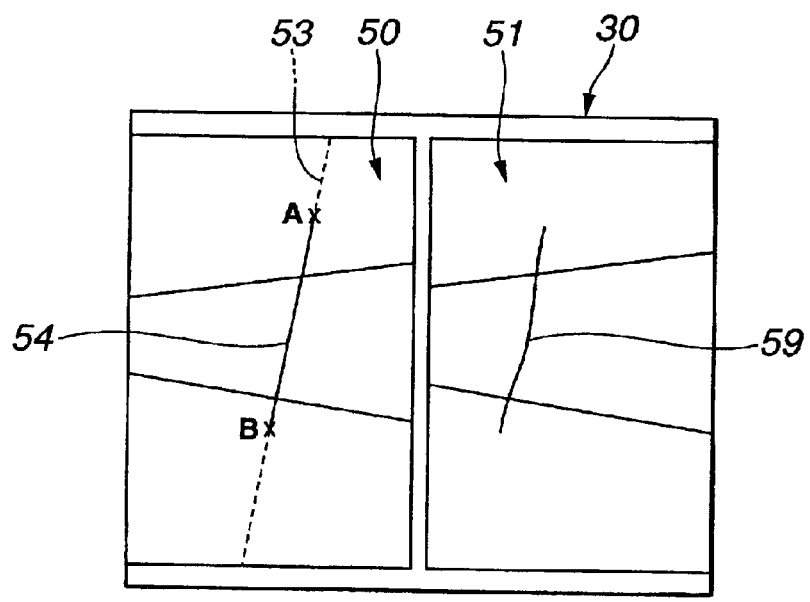

FIG. 1 to FIG. 15 are concerned with an embodiment of the present invention. FIG. 1 is an explanatory diagram schematically showing the configuration of an endoscope system capable of performing measurement. FIG. 2 is an explanatory diagram showing an imaging unit incorporated in the distal portion of an inserting section of an endoscope and a measuring device having an arithmetic unit. FIG. 3 shows a scene where an object-of-observation region is observed using an endoscope. FIG. 4 is a flowchart describing stereo measurement. FIG. 5 shows an example of an endoscopic image and a cutting-plane reference line displayed on the screen of a monitor by means of an image displaying means. FIG. 6 is an explanatory diagram concerning a cutting plane and a sectional contour line. FIG. 7 shows another example of a reference line. FIG. 8 shows an example of a sectional contour line displayed as section information. FIG. 9 is an explanatory diagram showing an example of a sectional contour line displayed while being superposed on a reference image. FIG. 10 is an explanatory diagram showing a camera coordinate system defined for presenting section information. FIGS. 11A and 11B show another example of a sectional contour line displayed as section information. FIG. 12 shows another example of a sectional contour line displayed as section information. FIG. 13 shows still another example of a sectional contour line displayed as section information. FIG. 14 is a flowchart for explaining an algorithm for searching for a corresponding point. FIG. 15 is an explanatory diagram showing screen images displayed on the monitor after searching for a corresponding point is completed.

As shown in FIG. 1, an endoscope system 1 for performing measurement according to the present embodiment consists mainly of an electronic endoscope 2 (hereinafter simply an endoscope) and a measuring device 3. An imaging unit for converging view images of an object-of-observation region on an imaging device that will be described later is incorporated in the endoscope 2. The measuring device 3 includes an arithmetic unit that performs image processing on image signals which represent the view images and are produced by the endoscope 2, and that performs various measurements using image data resulting from the image processing.

Incidentally, a light source unit (not shown) for supplying illumination light to an object of observation is incorporated in the measuring device 3. Endoscopic images of an object-of-observation region are displayed on the screen of a monitor 30.

The endoscope 2 has an elongated inserting section 20. An operating section 21 serving as a hand-held section is formed proximally to the inserting section 20. A universal cord 23 having a connector 22, which is freely attachable or detachable to or from the measuring device 3, fixed to the proximal end thereof is extended from the lateral surface of the operating section 21.

The inserting section 20 includes a distal portion 24, a bending portion 25, and a flexible portion 26 that are juxtaposed in that order from the distal end of the endoscope. An imaging optical system that will be described later is incorporated in the distal portion 24. The bending portion 25 has a plurality of bending pieces concatenated so that the pieces can revolve freely. The flexible portion 26 is formed with an elongated soft member. Note that a numeral 27 is referred to an operating knob 27 which is used to bend the bending portion 25.

As shown in FIG. 2, an imaging unit 40 composed of a pair of objective lens systems 41 and 42 and an imaging device 43 is incorporated in the distal portion 24. The imaging device 43 photoelectrically converts optical images, which are converged on the imaging surface thereof after passing through the objective lens systems 41 and 42, into image signals.

The inclusion of the objective lens systems 41 and 42 is intended to image an object-of-observation region while viewing it from a plurality of viewing points. Optical images passing through the objective lens systems 41 and 42 are converged on the imaging surface of the imaging device 43. In other words, the endoscope 2 employed in the present embodiment is a so-called stereoscopic endoscope that produces stereo images that cause a parallax.

As shown in FIG. 1 and FIG. 2, the measuring device 3 consists mainly of a camera control unit (hereinafter abbreviated as CCU) 31, a video capture circuit 32, a host computer 33, and a console 34. The CCU 31 converts image signals, which result from photoelectric conversion performed by the imaging device 43, into video signals according to which images are displayed on the monitor 30. The video capture circuit 32 converts the video signals, which are produced by the CCU 31, into digital image signals. The host computer 33 serving as an arithmetic unit uses the digital image signals produced by the video capture circuit 32 to perform arithmetic operations required for measurement. The console 34 is used to operate the measuring device 3 via the host computer 33.

As shown in FIG. 3, illumination light generated by the light source unit incorporated in the measuring device 3 is passed through the connector 22, and propagated over the universal cable 23 and light-guide optical fibers (not shown) that run through the inserting section 20. The illumination light is then emitted towards an object-of-observation region 4 through illumination windows 44. Consequently, endoscopic images of the object-of-observation region 4 are displayed on the monitor 30 of the measuring device 3.

Incidentally, according to the present embodiment, the console 34 is independent of a main unit 35 of the measuring device, and the monitor 30 is integrated with the main unit 35 of the measuring device. Depending on a purpose of use, however, the console 34 may respectively be integrated with or independent of the main unit 35 of the measuring device.

Referring to FIG. 4 to FIG. 24, actions to be performed and operations to be exerted when the endoscope system 1 having the foregoing components is used to perform stereo measurement will be described below.

For example, assume that the inserting section 20 of the endoscope 2 is inserted into a pipe, and the observation of the inside of the pipe is started to see if there is a corroded part or a flaw.

First, as shown in step S101 described in the flowchart of FIG. 4, view images of the object-of-observation region 4 illuminated by the illumination light are passed through the objective lens systems 41 and 42, and converged on the imaging surface of the imaging device 43 respectively. The view images on the imaging device 43 are photoelectrically converted into image signals. The respective image signals are transmitted to the CCU 31 incorporated in the measuring device 3 through the connector 22 over signal lines. The signal lines that are not shown are run through the inserting section 20, operating section 21, and universal cable 23.

The CCU 31 having received the image signals produces video signals. The video signals are transferred to the video capture circuit 32 and converted into digital image signals. As shown in step S102, the digital image signals are transferred to the host computer 33, while the image signals are transferred to the monitor 30, whereby the endoscopic view images are displayed on the screen of the monitor 30, as shown in step S103.

If a corroded part or the like is discovered during viewing of the monitor, the corroded part is measured. At this time, a viewer first uses the console 34 to select a stereo measurement mode. This causes the image displaying means incorporated in the host computer 33 to separately display a corrected reference image 50 and a corrected comparison image 51 on the monitor 30, as shown in FIG. 5. At this time, one of the endoscopic images of the view images picked up by the objective lens systems 41 and 42, for example, the image picked up by the objective lens system 41 is adopted as a reference image. The other image picked up by the other objective lens system 42 is regarded as a comparison image.

Incidentally, the images 50 and 51 are produced as the corrected images to be used for measurement by means of a corrected image producing means as shown in step S104. Specifically, the digital image signals fetched into the host computer 33 have distortions thereof corrected using a distortion correction coefficient pre-set in the imaging unit 40. The corrected reference image 50 and corrected comparison image 51 that are the corrected images to be used for measurement are used to perform stereo measurement, that is, to search for a corresponding point.

For measurement, as shown in step S105, two points A and B are firstly designated in the reference image 50 shown in FIG. 5 using a cutting-plane reference line designating means in order to draw a cutting-plane line that specifies a cutting-plane position which determines a section whose section information must be acquired for measurement. Specifically, for the operation, a viewer uses the console 34 or the like to move a pointer such as an arrow mark or a cursor that is displayed on the screen.

When the viewer designates the points A and B, a straight line passing through the points A and B as indicated with a dashed line in FIG. 5 is regarded as a cutting-plane reference line (hereinafter abbreviated as a reference line) 53. Otherwise, a segment linking the points A and B as indicated with a solid line therein is regarded as a cutting-plain reference segment (hereinafter abbreviated as a reference segment) 54. A cutting plane defined with the cutting-plane reference line 53 will be described in conjunction with FIG. 6. The image of the object of observation 4 is, in principle, converged as an inverted image opposite to the object of observation with an optical center between them. In the drawing, for a better understanding, the corrected reference image 50 is depicted as an erect image between the object of observation 4 and the optical center L.

Incidentally, aside from the reference line 53 drawn as mentioned above, another straight line indicated with a dot-dash line in FIG. 7 may be drawn as an auxiliary line 55 that is another reference line. The auxiliary line 55 meets the reference line 53 at a certain angle (crosses the reference line 53 at right angles in the drawing) at a point interposed between the points A and B (middle point in the drawing).

A viewer's intended cutting plane 56 is a plane indicated with an alternate long and two short dashes line and orthogonal to the corrected reference image 50 shown in the figure. The cutting plane 56 is defined as a plane containing the reference line 53 and the optical center L of the optical system that picks up the reference image.

Points A1 and B1 in the figure are mapped points on the surface of the object-of-observation region 4 resulting from mapping of the points A and B in the corrected reference image 50. That is, a sectional contour line 57 that is an object of display in the present embodiment is defined as a line shared by the surface of the object-of-observation region 4 seen from a viewing point and the cutting plane 56.

Subsequently, the optical axis of the reference image optical system is projected as a point on the corrected reference image 50, and the point serves as the image center O of the corrected reference image 50. Incidentally, a numeral 58 is referred to an optical axis 58 which is shown as a dot-dash line linking the image center O and the optical center L in FIG. 6.

As shown in step S106, all pixels lying along the reference line 53 (or the reference segment 54) in the corrected reference image 50 that is a corrected image to be used for measurement are regarded as points of attention in order to acquire section information concerning a section determined with the cutting plane 56. Therefore, as shown in step S107, a corresponding point searching means searches for a corresponding point, that is, a pixel in the corrected comparison image 51 associated with each point of attention. Consequently, a group of corresponding points 59 that will be described later is sampled. An algorithm for searching for a corresponding point will be described later in conjunction with a flowchart in FIG. 14 and FIG. 15.

If corresponding points are found at step S107 of corresponding point search, control is passed to step S108. A difference between the position of each point of attention in the corrected reference image 50 and the position of its corresponding point in the corrected comparison image 51 is calculated, that is, a parallax of each point of attention relative to its corresponding point is calculated. Control is then passed to step S109. Based on the calculated parallax and optical data, a section information arithmetic means calculates three coordinates representing a point in three-dimensional space that results from mapping of each point of attention. The optical data includes a base length that is a distance between the optical centers of the optical systems and is calculated in advance, the focal lengths relevant to the optical systems, and coordinates representing each of mapped points in the corrected image to be used for measurement resulting from mapping of the optical axes of the optical systems.

If three coordinates representing each point, that is, all pixels lying along the reference line 53 are calculated at step S109, control is passed to step S110. Based on the three coordinates of each point, section information concerning a section determined with the cutting plane 56 is constructed in a viewer's desired manner by selecting any of four display forms described later. Control is then passed to step S111. A section information outputting means displays, as a contour line outlining a section, section information that assists in readily grasping the outline of a section of an object of observation on the screen of the monitor 30. Incidentally, when the contour line outlining a section is displayed on the screen of the monitor 30, only the contour line may be displayed on behalf of the corrected reference image 51 on the screen. Otherwise, another window may be displayed on the screen and the contour line may be displayed within the window. Otherwise, the contour line may be superposed on the corrected reference image 50.

Now, the section information and the algorithm for searching for a corresponding point will be described below.

To begin with, section information will be described. The section information may be displayed in any of four display forms described below.

(1) Directly Displaying Section Information Concerning a Section Determined with a Cutting Plane Section information is displayed as a contour line 57a outlining a section as shown in FIG. 8. In the figure, the axis of ordinates represents an orthogonal projection of the reference segment 54 or reference line 53 on the cutting plane 56, and the axis of abscissas represents an orthogonal projection of the optical axis 58 on the cutting plane 56. In this case, the contour line outlining the section is rendered linearly.

In order to display the contour line 57a outlining the section on the screen of the monitor 30 during measurement, another window may be opened on the monitor and the contour line 57a outlining the section may be displayed within the window. Otherwise, the contour line 57a outlining the section may be, as shown in FIG. 9, superposed on the reference image 50 displayed on the monitor 30. Incidentally, when the contour line is superposed on the reference image, an arrow mark C or the like is displayed as a mark indicating the direction of a viewing point. The mark helps learn the irregularity of the contour line.

(2) Projecting Section Information on a Plane in Space

As shown in FIG. 10, a camera coordinate system is defined as a coordinate system having an origin thereof aligned with the optical axis L of the optical system that picks up the reference image 50. Moreover, the x axis of the coordinate system is extended horizontally rightwards towards the object-of-observation surface 52, the y axis thereof is extended vertically upwards, and the z axis thereof is extended in a depth direction. Section information is projected on the xz plane shown in FIG. 11A or the yz plane shown in FIG. 11B, whereby a contour line 57b or 57c outlining the section is displayed. In this display form, the same projection technique as the one employed in plotting a normal projection drawing can be adopted. It is therefore advantageous that a viewer accustomed to the projection technique for plotting a normal projection drawing can easily grasp the outline of a section. Note that coordinate axes or a plane of projection can be defined arbitrarily depending on a purpose of use.

(3) Displaying Section Information Quasi Three-Dimensionally

As shown in FIG. 12, a viewing point other than a viewing point from which a line of sight extends through the endoscope 2 is newly set in real space. A contour line 57d outlining a section seen from the set viewing point is displayed. A cylindrical graphic in the drawing represents the position of the endoscope 2 in the space for better comparison. Moreover, an image three-dimensionally expressing the position of the viewing point may be simultaneously displayed on another screen. In this display form, the viewing point is shifted sequentially in order to change the apparent position of a section. Consequently, the three-dimensional outline of an object of observation can be grasped intuitively.

(4) Displaying Section Information by Sampling a Depth that is a Distance from a Reference Line Defined in Real Space As shown in FIG. 8 and FIG. 13, a distance from a point D1 to a point D2 is indicated with a line perpendicular to the reference segment 54 in the corrected reference image 50. The point D1 is a point on the surface of the object of observation 4 resulting from mapping of the point D on the reference segment 54 or reference line 53. The point D2 is a point on a line A1B1 linking points A1 and B1, which are points in real space resulting from mapping of the points A and B, resulting from mapping of the point D. The point D is set to all points lying along the reference segment 54 or reference line 53, whereby a contour line 57e outlining a section is displayed. According to this displaying technique, as described in the paragraph (1), an arrow mark C indicating the direction of a viewing point is displayed as a cue to learn the irregularity in the outline of a section. Incidentally, the sectional contour line 57e may be colored depending on the length of the segment D1D2 in order to provide the cue.

This displaying technique can compactly display a result even with a contour line whose depth varies outstandingly.

Next, the algorithm for searching for a corresponding point will be described below.

Searching for a corresponding point is always performed in a corrected image to be used for measurement. Searching for a corresponding point is known as template matching or window matching, where an algorithm for searching for a corresponding point using information of points surrounding a point of attention is employed.

A straight line in space that is projected as a point on the corrected reference image 50 is projected as a straight line on the corrected comparison image 51. The straight line is referred to as an epi-polar line. A corresponding point in the corrected comparison image 51 associated with a point of attention in the corrected reference image 50 theoretically lies only on the epi-polar line. Therefore, searching for a corresponding point should be performed on a domain containing the epi-polar line and several pixels above and below the epi-polar line in consideration of an error. Therefore, a searching procedure is described in the flowchart of FIG. 14.

First, searching for a corresponding point is started as shown in step S107. Consequently, a domain P1 is defined to contain a point of attention as shown in step S201. Control is then passed to step S202 where an epi-polar line relevant to the point of attention is calculated. Points belonging to a domain that contains the epi-polar line and several pixels above and below the epi-polar line are sampled as candidates for a corresponding point.

Next, control is passed to step S204 where a domain P2 whose size is the same as the size of the domain P1 containing the point of attention is defined to contain each candidate. A coefficient of mutual correlation between the normalized powers of the domain P1 containing the point of attention and the domain P2 containing each candidate for a corresponding point is calculated or the square of the difference between the powers is calculated. Thus, the degree of correspondence by which the candidate corresponds to the point of attention is calculated. As shown in steps S206 and S207, the degrees of correspondence of all the candidates are calculated, and the calculated degrees of correspondence are preserved in relation to all the candidates. After preserving the calculated degrees of correspondence of all the candidates is completed, the candidate exhibiting the highest degree of correspondence is adopted as a corresponding point associated with the point of attention as shown in steps S208 and S209. If it is judged at step S210 that the corresponding points associated with all the candidates have been searched for, corresponding point search is completed. Control is then passed to step S108.

Through the corresponding point search, a corresponding point associated with each of the points of attention lying along the reference segment 54 in the corrected reference image 50 are sampled as described in FIG. 14. When the corresponding points associated with all the points of attention have been searched for, the group of corresponding points 59 that is a set of corresponding points is displayed on the corrected comparison image 51.

As described above, a cutting-plane reference line can be drawn in order to specify the position of a section a viewer wants to observe, by selecting a stereo measurement mode and designating two points in a reference image displayed on the screen of the monitor during observation.

Moreover, the viewer can easily grasp the outline of the section by displaying section information concerning a section determined with the cutting-plane reference line drawn by a viewer as a contour line outlining the section on the screen of the monitor in the viewer's desired display form.

This enables the viewer to swiftly specify an observed portion, to intuitively grasp the outline of a section of the specified observed portion and to shortly complete observation in case a corroded part or the like is found during observation.

When a range of points within which a corresponding point is searched for may be limited to a cutting-plane reference segment but not to a cutting-plane reference line. This leads to a further reduction in the time required to complete searching for a corresponding point.

Moreover, according to the present embodiment, corresponding points associated with all points of attention lying along the reference line 53 or reference segment 54 are searched for. It is essentially ambiguous to how the reference image 50 is associated with the comparison image 51. It is therefore hard to associate a point within an occlusive domain or a point adjoining the occlusive domain with another point. The occlusive domain refers to a domain whose power has no difference from that of a surrounding domain, a domain containing pixels that are visible in the reference image but invisible in the comparison image, or a domain containing pixels that are invisible in the reference image but visible in the comparison image.

Consequently, there is a fear of taking an incorrect point for a corresponding point. If an incorrect point is taken for a corresponding point, a noise is contained in position information concerning the group of corresponding points 59 to be displayed. In some cases, the outline of an object of observation may be judged incorrectly.

Therefore, a plurality of approaches that will be described below has been devised in efforts to exclude a point that may be associated with an incorrect one or to improve precision in association. Consequently, precision in acquired section information can be improved.

A description will be made of the approaches to reduce ambiguousness in associating one point in one image with another point in another image.

(1) A method of improving precision in section information by utilizing the order of points lying along a reference line will be described with reference to the flowcharts of FIG. 16 and FIG. 17.

Figure 16:
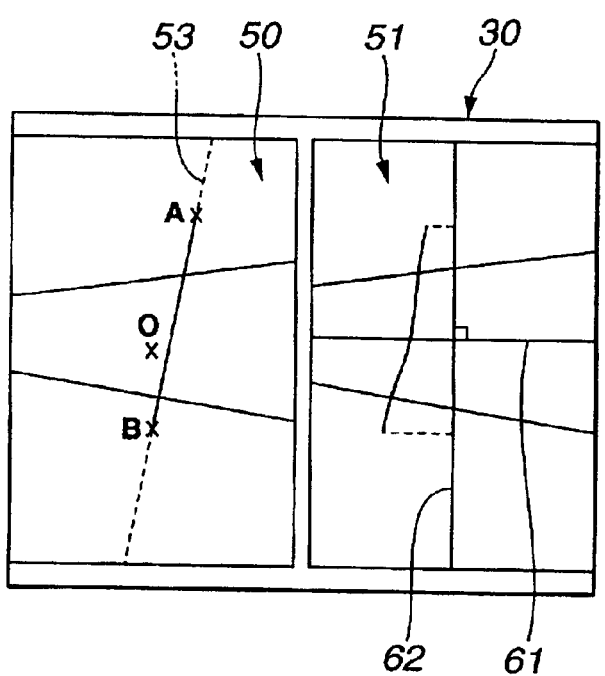
FIG. 16 to FIG. 22 are explanatory diagrams concerning the approaches to reduce ambiguousness in association between a plurality of images.
Figure 17:
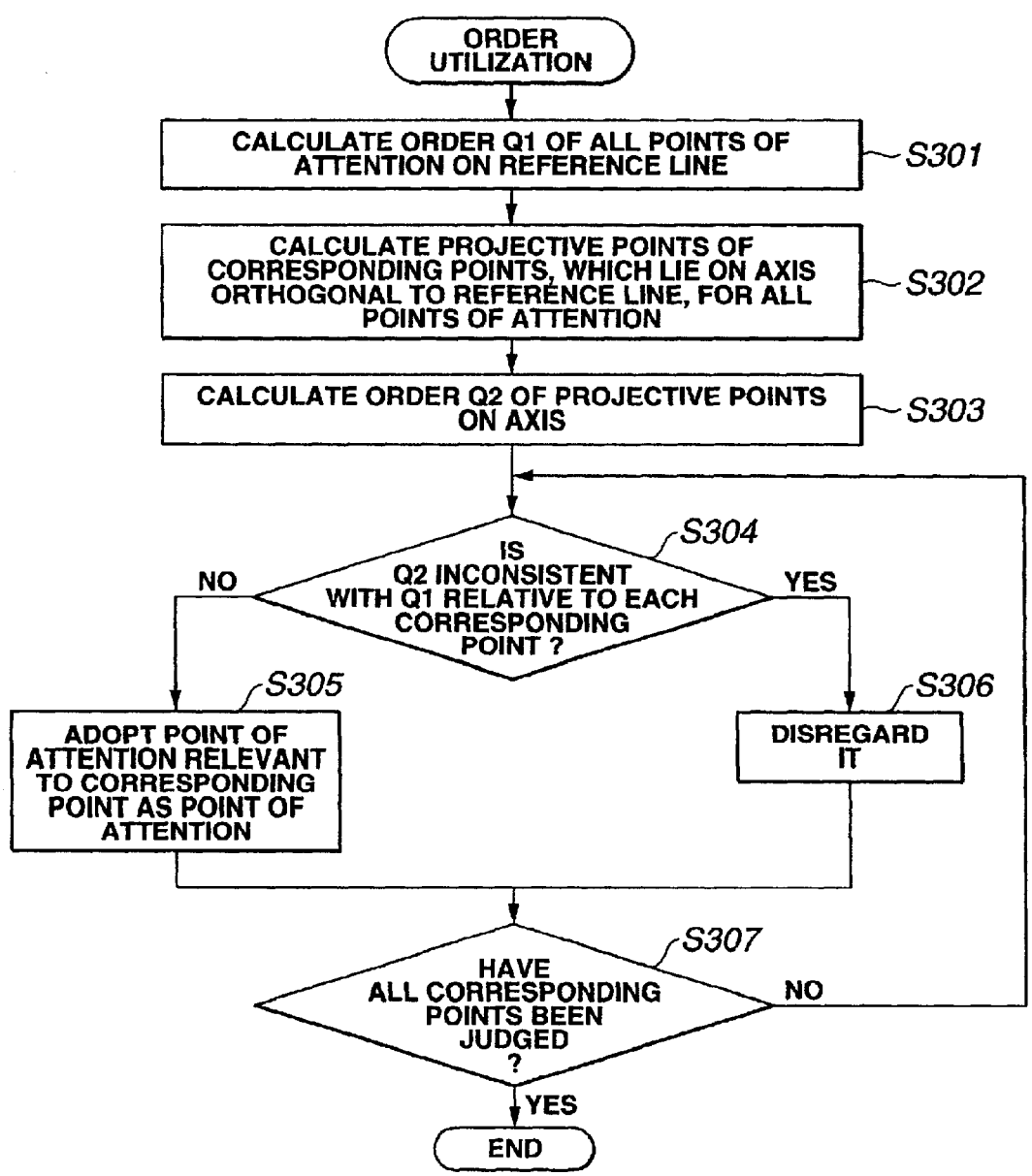

As described in the flowcharts of FIG. 16 and FIG. 17, at step S301, the order of all points of attention lying along the reference line 53 is detected. The order shall not change even if the reference line 53 is projected onto an axis orthogonal to a base line and parallel to the imaging surface of the imaging device. The base line is a straight line linking the optical center of the optical system that picks up the reference image and the optical center of the optical system that picks up the comparison image. The projection is the same as the projection of the reference line 53 onto an axis 62 in the reference image 51 that is orthogonal to an epi-polar line 61 corresponding to the image center O of the reference image 50.

Consequently as shown in step S302, projected points on the axis 62 onto which the corresponding points associated with all points of attention are projected are detected. Control is then passed to step S303. The order of the projected points on the axis 62 is then detected.

As shown in steps S304, S305, and S306, it is judged whether the order of the points of attention is inconsistent with the order of the projected points of the corresponding points. A point of attention whose order is inconsistent with the order of the projected point of the corresponding point thereof is regarded as a point that has been unsuccessfully associated with another and then disregarded. In contrast, a point of attention whose order is consistent with the order of the projected point of the corresponding point thereof is adopted. In other words, for example, assume that points of attention a, b, c, d, and e are juxtaposed in that order along the reference line. If the projected points of the corresponding points are juxtaposed in order of a, b, d, c, and e, the points of attention d and c are disregarded because their orders are inconsistent with the orders of the projected points of the corresponding points thereof.

The above processing is performed as a step interposed between steps S106 and S107 in the flowchart of FIG. 4. Step S107 and subsequent steps are performed only on adopted points.

Figure 18:
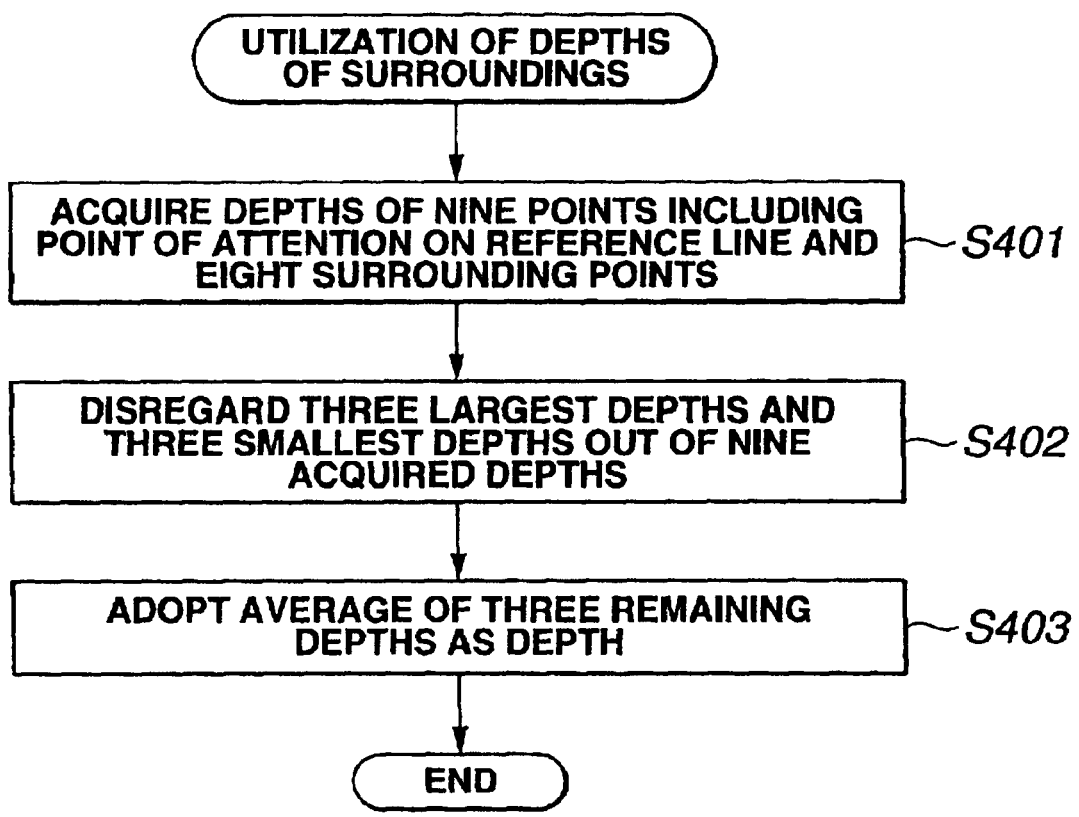

(2) A method of improving precision in section information by utilizing depths of surrounding points will be described with reference to the flowchart of FIG. 18.

First, a range of points from which points of attention are sampled at step S106 is extended to contain pixels adjoining the points of attention. In other words, as shown in step S401 in FIG. 18, the total of nine points including a point of attention on the reference line 53 and eight surrounding points are associated with other points.

As shown in steps S402 and S403, the average of three intermediate depths (other than three largest depths and three smallest depths) among the depths of the nine points, that is, a median is adopted as the depth of the point of attention. This processing is a kind of low-pass filtering and is performed as a step interposed between step S109 and step S110 in the flowchart of FIG. 4.

(3) A method of improving precision in section information by utilizing back-corresponding points will be described with reference to the flowchart of FIG. 19.

Figure 19:
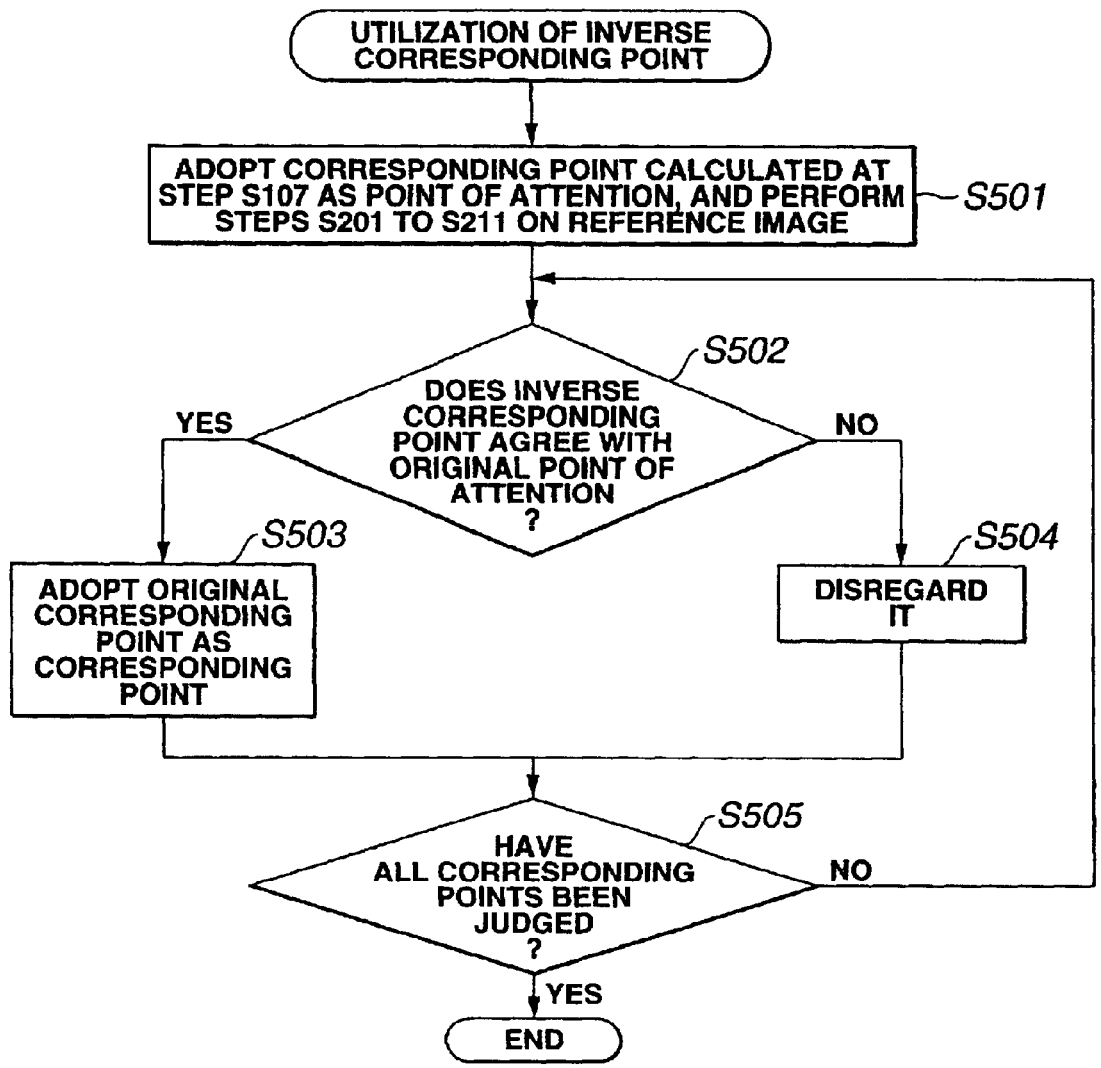

After a corresponding point associated with a certain point of attention in the corrected reference image 50 is detected in the corrected comparison image 51 at step S107, the corresponding point in the corrected comparison image 51 is back-associated with a point in the corrected reference image 50 as shown in step S501 in FIG. 19 according to a sequence described in the flowchart of FIG. 14.

As shown in steps S502, S503, S504, and S505, it is judged that the back-corresponding point corresponds to the original point of attention. A back-corresponding point that does not correspond to a point of attention is regarded as a point that has been unsuccessfully associated with another point and disregarded. A back-corresponding point that corresponds to a point of attention is adopted. This processing is performed as a step interposed between step S107 and step S108 in FIG. 4. Step S108 and subsequent steps are performed only on adopted points.

Figure 20:
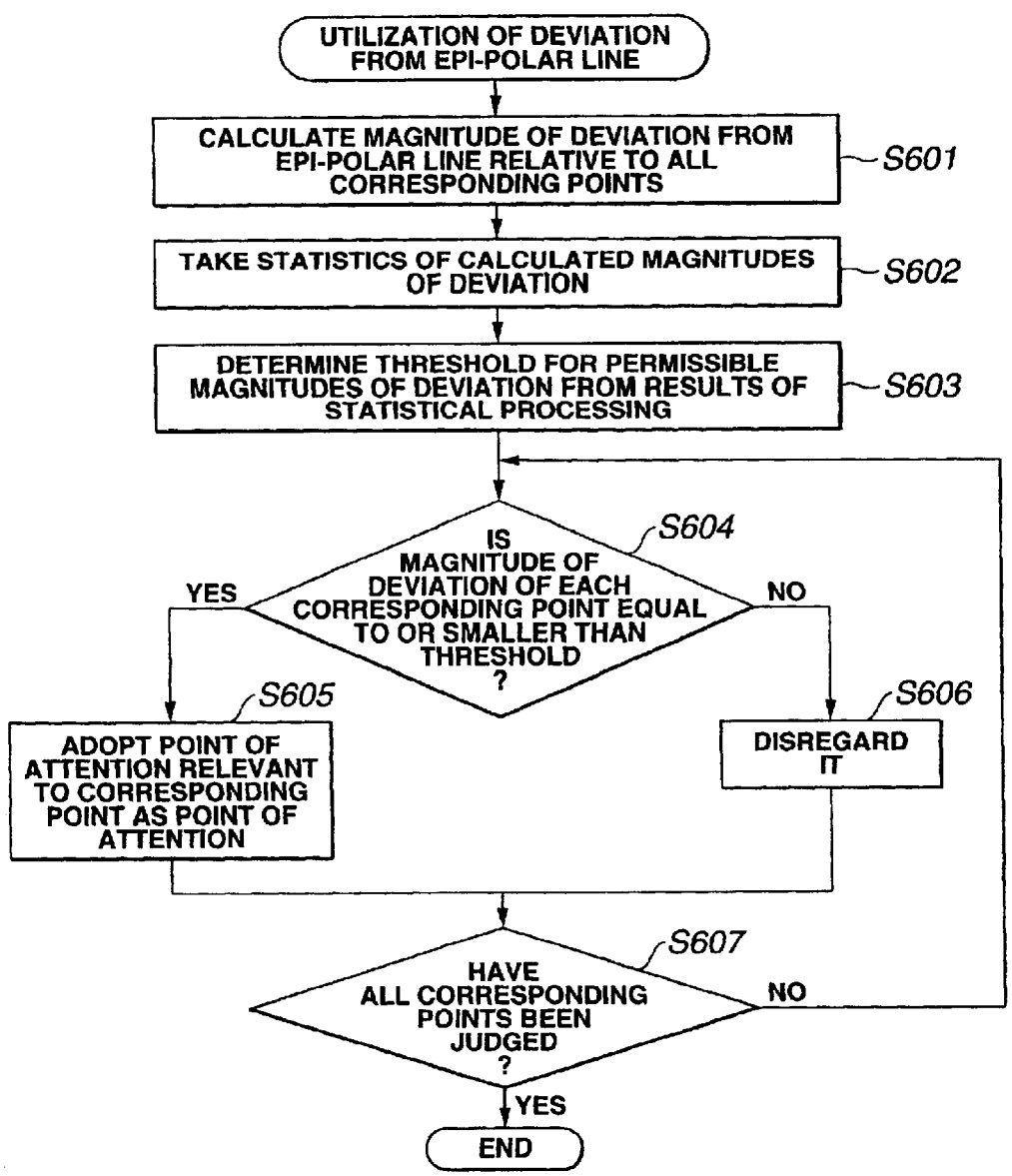

(4) A method of improving precision in section information by utilizing the magnitude of deviation from an epi-polar line will be described with reference to the flowchart of FIG. 20.

The deviation of a corresponding point in the corrected reference image 51, which results from association, from an epi-polar line can exhibit a certain trend. Based on this theory, the magnitudes of deviation of all corresponding points are detected as shown in step S601 described in FIG. 20. Then as shown in step S602, the detected magnitudes of deviation are statistically processed. As shown in step S603, the trend of the magnitudes is inferred from the results of the statistical processing, and a threshold indicating a maximum permissible magnitude of deviation is determined.

Thereafter, as shown in steps S604, S605, S606, and S607, a point of attention relevant to a corresponding point whose magnitude of deviation exceeds the threshold is regarded as a point that has been unsuccessfully associated with another and disregarded. A point of attention relevant to a corresponding point whose magnitude of deviation is equal to or smaller than the threshold is adopted. This processing is performed as a step interposed between step S107 and step S108 described in FIG. 4. Step S108 and subsequent steps are performed only on adopted points of attention.

(5) A method of improving precision in section information by utilizing a differential coefficient will be described with reference to the flowchart of FIG. 21.

Association is likely to succeed when the power of a domain containing a point of attention changes but is hard to succeed when the power thereof does not change. Therefore, points of attention are selected from a domain whose power changes. This leads to a reduction in ambiguousness in association.

Figure 21:
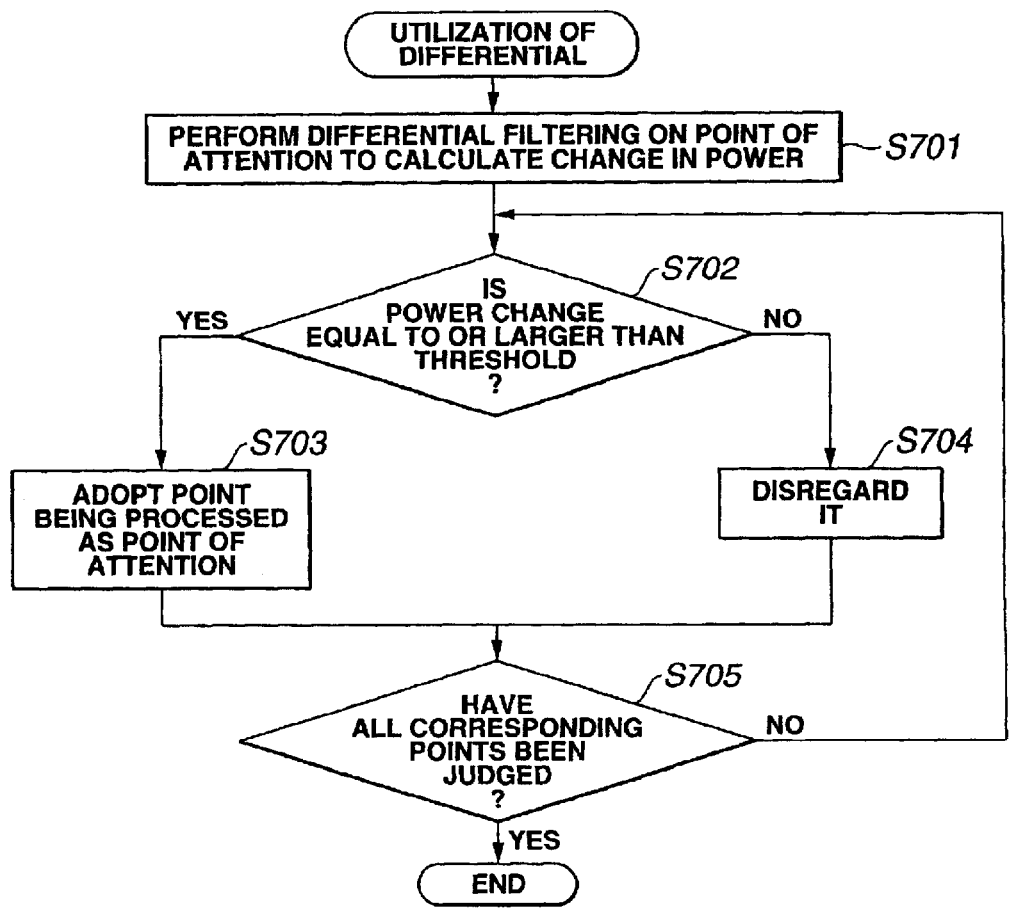
Figure 22:
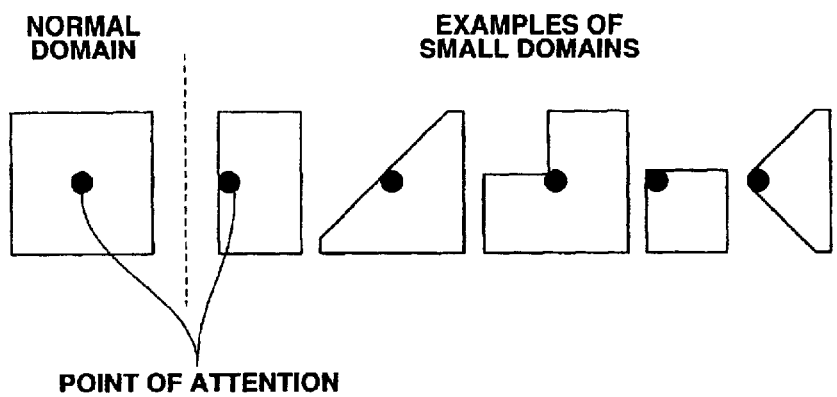

Namely, differential filtering is performed on a domain containing a point of attention in order to calculate a change in the power of the domain as shown in step S701 in FIG. 21.

As shown in steps 702, 703, 704, and 705, it is judged whether the power change is equal to or larger than a threshold and thus detected whether the power has changed. If the power change is less than the threshold, the point of attention is disregarded. If the power change is equal to or larger than the threshold, the point of attention is adopted. In other words, only a corresponding point that is associated with a pixel contained in a domain whose power is judged to have changed is searched for. This processing is performed as a step interposed between step 106 and step 107 described in FIG. 4. Step 107 and subsequent steps are performed only on adopted points of attention.

(6) A method of improving precision in section information by adjusting the shape of a domain containing a point of attention will be described below.

If a point of attention adjoins an occlusive domain, the occlusive domain may overlap a domain defined to contain the point of attention and used for searching. This leads to ambiguous association. Therefore, small domains in each of which the point of attention lies on the perimeter thereof are defined, and a candidate for a corresponding point associated with the point of attention is searched for within each small domain. The degree of correspondence exhibited by the candidate is then detected. Consequently, the highest degree of correspondence exhibited by any candidate for the corresponding point is adopted as the degree of correspondence by which the corresponding point corresponds to the point of attention. Examples of small domains are shown by the right-hand side of a border line indicated with a dashed line in FIG. 22. Black dots in the drawing indicate points of attention. A normally defined domain is shown by the left-hand side of the border line.

One of the aforesaid six methods is used or two or more of the aforesaid six methods are arbitrarily used in combination in order to acquire section information, whereby high-precision section information can be acquired.

Figure 23:
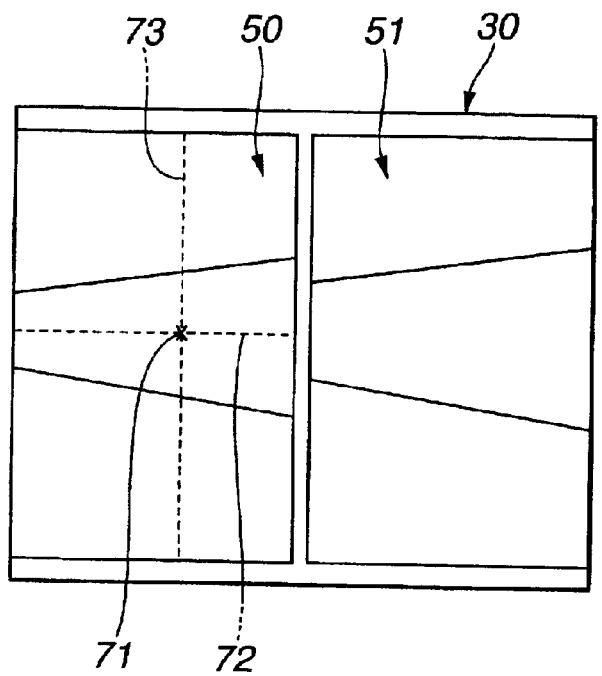
FIG. 23 is an explanatory diagram showing an example of a reference line defined by designating one point.
Figure 24:
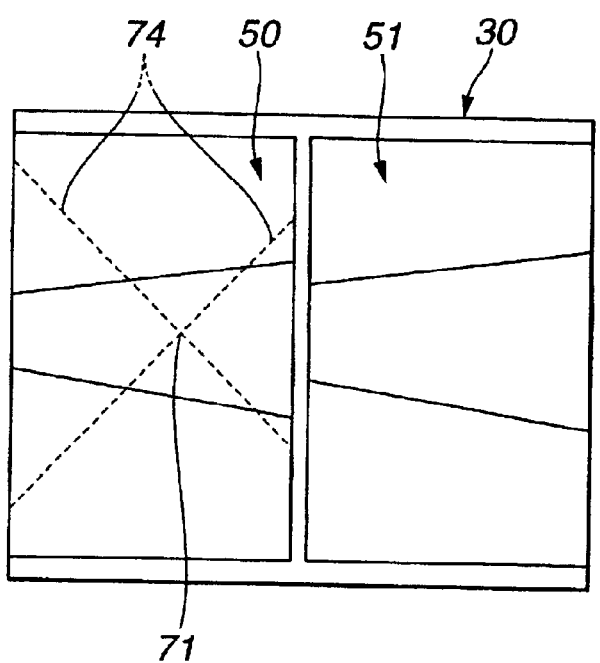
FIG. 24 is an explanatory diagram showing another example of a reference line defined by designating one point.

Moreover, instead of acquiring section information by designating two points as mentioned above, one point in the corrected reference screen image 50A may be adopted as a sole reference point 71 as shown in FIG. 23 and FIG. 24. A straight line passing through the reference point 71 may then be adopted as a reference line. Section information may thus be acquired.

Incidentally, the reference line may be defined as a line described below.

(1) Line 72 shown in FIG. 23, that is, a line passing through the designated reference point 71 and being parallel to the horizontal direction of the screen of the monitor 30

(2) Line 73 shown in FIG. 23, that is, a line passing through the designated reference point 71 and being parallel to the vertical direction of the screen of the monitor 30

(3) Lines 72 and 73, that is, lines passing through the designated reference point 71 and being parallel to the horizontal and vertical directions of the screen of the monitor 30

(4) Line 74 shown in FIG. 24, that is, a line passing through the designated reference point 71 and meeting the two straight lines 72 and 73 at any angles Thus, one point is designated in order to define a reference line. This results in simpler operation. A place whose sectional outline must be inspected can be designated directly.

Although an example using two images is explained in the present embodiment, three or more images may also perform a section display.

Moreover, as the second embodiment, images to be displayed in a stereo measurement mode may be employed as a reference image and a comparison image that are not corrected in place of the corrected reference image 50 and corrected comparison image 51. A reference line then may be drawn in the reference image. Consequently, production of corrected images to be used for measurement can be simplified. The time required to select the stereo measurement mode can be shortened drastically. Note that the other operations and advantages are identical to those of the first embodiment.

Having described the preferred embodiments of the present invention by referring to the accompanying drawings, it should be understood that the present invention is not limited to the embodiments but a person skilled in the art can make various changes and modifications without departing from the spirit or scope of the invention defined in the appended claims.

What is claimed is:

1. An endoscope system having an imaging unit that images an object of observation while viewing it from a plurality of viewing points, performing image processing and arithmetic operations on image signals that represent images that the imaging unit picks up while viewing the object of observation from the viewing points, and thus achieving stereo measurement, said endoscope system comprising:

a corrected image producing means for adopting one of the images, which are picked up by viewing the object of observation from the plurality of viewing points, as a reference image, regarding the other image as a comparison image, correcting optical distortions in the reference image and comparison image, and thus producing a corrected reference image and a corrected comparison image;

an image displaying means for displaying on a screen at least the reference image or corrected reference image;

a cutting-plane reference line designating means for use in drawing a cutting-plane reference line, which specifies a cutting-plane position that determines a section of the object of observation whose section information is desired to be acquired, in the image displayed on the screen;

a corresponding point searching means for regarding a point, which lies on the cutting-plane reference line in the corrected reference image, as a point of attention, and searching the corrected comparison image for a corresponding point that is associated with the point of attention;

a section information arithmetic means for calculating three coordinates, which represent a point in three-dimensional space whose mapping results in a corresponding point on the cutting-plane reference line according to the principles of trigonometric measurement, using the position of the point of attention in the corrected reference image and the position of the corresponding point in the corrected comparison image for acquiring section information concerning a section of the object of observation determined with the cutting-plane position; and a section information outputting means for providing section information according to the coordinates calculated by said section information arithmetic means.

2. An endoscope system according to claim 1, wherein the images to be displayed include at least the reference image, and the cutting-plane reference line is drawn in the reference image.

3. An endoscope system according to claim 1, wherein the images to be displayed include at least the corrected reference image, and the cutting-plane reference line is drawn in the corrected reference image.

4. An endoscope system according to claim 1, wherein the cutting-plane reference line is drawn using a pointer that is displayed while being superposed on the reference image or the correct reference image.

5. An endoscope system according to claim 4, wherein once the pointer is used to designate at least one point, the cutting-plane reference line is drawn.

6. An endoscope system according to claim 1, wherein the section information provided by said section information outputting means is a contour line outlining a section.

7. An endoscope system according to claim 1, wherein:

the corresponding point searching means searches the corrected comparison image for the corresponding point that is associated with the point of attention by identifying a plurality of candidate points of the corrected comparison image, determining a degree of correspondence of each of the plurality of candidate points to the point of attention, and selecting the candidate point with the highest degree of correspondence as the corresponding point.

8. An endoscope system according to claim 7, wherein:

the plurality of candidate points are identified according to a domain of the corrected comparison image that contains an epi-polar line and a number of surrounding pixels, where the epi-polar line is a straight line that is projected from the point of attention on the corrected reference image to the corrected comparison image.

9. An endoscope system according to claim 1, wherein:

the corresponding point searching means regards a plurality of points, which lie on the cutting-plane reference line in the corrected reference image, as a corresponding plurality of points of attention, and searches the corrected comparison image for a corresponding plurality of points that are associated with the plurality of points of attention;

for each of the plurality of points of attention, the section information arithmetic means calculates three coordinates, which represent a point in three-dimensional space whose mapping results in a corresponding point on the cutting-plane reference line according to the principles of trigonometric measurement, using the position of the point of attention in the corrected reference image and the position of the corresponding point in the corrected comparison image to acquire the section information; and the section information outputting means provides the section information according to the coordinates calculated by said section information arithmetic means.

10. An endoscope system according to claim 9, wherein:

the cutting-plane reference line designating means draws the cutting-plane reference line responsive to a viewer input that designates two points in the reference image or corrected reference image displayed on the screen;

the two points define a segment of the cutting-plane reference line; and the plurality of points of attention are limited being along the segment.

11. An endoscope system according to claim 1, wherein:

the cutting-plane reference line designating means draws the cutting-plane reference line responsive to a viewer input that designates two points in the reference image or corrected reference image displayed on the screen to thereby specify the cutting-plane reference line and the cutting-plane position.

12. An endoscope system according to claim 1, wherein:

the cutting-plane reference line designating means draws the cutting-plane reference line responsive to a viewer input that designates two points in the reference image or corrected reference image displayed on the screen;

the two points define a segment of the cutting-plane reference line; and the point of attention is limited to being along the segment.

13. An endoscope system having an imaging unit that images an object of observation while viewing it from a plurality of viewing points, performing image processing and arithmetic operations on image signals that represent images that the imaging unit picks up while viewing the object of observation from the viewing points, and thus achieving stereo measurement, said endoscope system comprising:

a corrected image producing component for adopting one of the images, which are picked up by viewing the object of observation from the plurality of viewing points, as a reference image, regarding the other image as a comparison image, correcting optical distortions in the reference image and comparison image, and thus producing a corrected reference image and a corrected comparison image;

an image displaying component for displaying on a screen at least the reference image or corrected reference image;

a cutting-plane reference line designating component for use in drawing a cutting-plane reference line, which specifies a cutting-plane position that determines a section of the object of observation whose section information is desired to be acquired, in the image displayed on the screen;

a corresponding point searching component for regarding a point, which lies on the cutting-plane reference line in the corrected reference image, as a point of attention, and searching the corrected comparison image for a corresponding point that is associated with the point of attention;

a section information arithmetic component for calculating three coordinates, which represent a point in three-dimensional space whose mapping results in a corresponding point on the cutting-plane reference line according to the principles of trigonometric measurement, using the position of the point of attention in the corrected reference image and the position of the corresponding point in the corrected comparison image for acquiring section information concerning a section of the object of observation determined with the cutting-plane position; and a section information outputting component for providing section information according to the coordinates calculated by said section information arithmetic component.

* * * * *